(12) United States Patent
Besnoin et al.

(10) Patent No.: US 10,406,866 B2
(45) Date of Patent: Sep. 10, 2019

(54) TIRE SENSOR FOR A TIRE MONITORING SYSTEM

(71) Applicant: The Goodyear Tire & Rubber Company, Akron, OH (US)

(72) Inventors: Etienne Besnoin, Luxembourg (LU); Armand René Gabriel Leconte, Bigonville (LU); Sebastien Willy Fontaine, Vichten (LU); Frederic Ngo, Blaschette (LU); Claude Bach, Everlange (LU); Jean-Claude Kreutz, Boxhorn (LU); Patrick François Willems, Mersch (LU); Kanwar Bharat Singh, Stow, OH (US); Anthony William Parsons, Domeldange (LU)

(73) Assignee: The Goodyear Tire & Rubber Company, Akron, OH (US)

( * ) Notice: Subject to any disclaimer, the term of this patent is extended or adjusted under 35 U.S.C. 154(b) by 614 days.

(21) Appl. No.: 15/083,356

(22) Filed: Mar. 29, 2016

(65) Prior Publication Data

US 2017/0246915 A1 Aug. 31, 2017

Related U.S. Application Data

(60) Provisional application No. 62/300,194, filed on Feb. 26, 2016.

(51) Int. Cl.
*G01M 17/02* (2006.01)
*B60C 11/24* (2006.01)
(Continued)

(52) U.S. Cl.
CPC ........ *B60C 11/246* (2013.01); *B60C 23/0415* (2013.01); *B60C 23/0488* (2013.01); *G01M 17/02* (2013.01); *G01N 3/56* (2013.01)

(58) Field of Classification Search
CPC .............. B60C 11/246; B60C 23/0415; B60C 23/0488; G01M 17/02; G01N 3/56
(Continued)

(56) References Cited

U.S. PATENT DOCUMENTS

| 5,483,827 A | 1/1996 | Kulka et al. |
| 6,441,728 B1 | 8/2002 | Dixit et al. |

(Continued)

FOREIGN PATENT DOCUMENTS

| CN | 101498621 | 8/2009 |
| CN | 103057361 | 4/2013 |

(Continued)

OTHER PUBLICATIONS

European Search Report dated Jul. 5, 2017 for Application Serial No. EP17157807.

*Primary Examiner* — Vu A Le
(74) *Attorney, Agent, or Firm* — Robert N. Lipcsik

(57) ABSTRACT

An assembly determines operating parameters of a tire. The assembly includes a tripod sensor mounted within an inner cavity of the tire underneath a crown portion and an innerliner on which the tripod sensor is mounted. The tripod sensor includes a tri-axial accelerometer for creating a circumferential signal for determining slip ratio, a lateral signal for determining a slip angle, and a radial signal for determining load on the tire.

12 Claims, 5 Drawing Sheets

(51) Int. Cl.
  *B60C 23/04* (2006.01)
  *G01N 3/56* (2006.01)
(58) Field of Classification Search
  USPC .................................. 73/146, 146.2, 146.3
  See application file for complete search history.

(56) References Cited

U.S. PATENT DOCUMENTS

| | | |
|---|---|---|
| 6,549,125 B2 | 4/2003 | Nigon et al. |
| 6,631,637 B2 | 10/2003 | Losey |
| 6,725,713 B2 | 4/2004 | Adamson et al. |
| 6,851,308 B2 | 2/2005 | Fonteneau |
| 8,166,809 B2 | 5/2012 | Weston |
| 8,707,756 B2 | 4/2014 | Shiozawa |
| 9,050,864 B2 | 6/2015 | Singh et al. |
| 9,061,662 B2 | 6/2015 | Haas |
| 9,199,516 B2 | 12/2015 | Jansen |
| 2002/0188392 A1 | 12/2002 | Breed et al. |
| 2003/0056579 A1 | 3/2003 | Poulbot et al. |
| 2005/0072223 A1* | 4/2005 | Fennel ................... B60C 23/061 73/146.2 |
| 2005/0085987 A1* | 4/2005 | Yokota ................ B60C 23/0477 701/80 |
| 2005/0103100 A1 | 5/2005 | Miyoshi et al. |
| 2005/0150283 A1* | 7/2005 | Shick ...................... B60C 11/24 73/146 |
| 2011/0040464 A1* | 2/2011 | Ono ........................ G01C 19/00 701/70 |
| 2014/0366618 A1* | 12/2014 | Singh ...................... B60C 23/04 73/146.3 |
| 2018/0370301 A1* | 12/2018 | Sekizawa ............ B60C 23/0493 |

FOREIGN PATENT DOCUMENTS

| | | |
|---|---|---|
| CN | 104057790 | 9/2014 |
| EP | 2813378 A1 | 12/2014 |
| WO | 2012023379 A1 | 2/2012 |

\* cited by examiner

TIRE SENSOR FOR A TIRE MONITORING SYSTEM

FIELD OF THE INVENTION

The present invention generally relates to tire sensors. More particularly, the present invention directed to tire monitoring systems for collecting measured tire parameter data during vehicle operation.

BACKGROUND OF THE INVENTION

The incorporation of electronic devices with pneumatic tire structures yields many practical advantages. Tire electronics may include sensors and other components for obtaining information regarding various physical parameters of a tire, such as temperature, pressure, number of tire revolutions, vehicle speed, etc. Such performance information may be useful in tire monitoring and warning systems, and may have potential use as a part of a feedback system to regulate or control certain tire and/or vehicle related systems.

Another potential capability offered by electronics systems integrated with tire structures corresponds to asset tracking and performance characterization for commercial vehicular applications. Commercial truck fleets, aviation crafts, and earthmover/mining vehicles are all viable industries that could utilize the benefits of tire electronic systems and related information transmission. Tire sensors may determine the distance each tire in a vehicle has traveled and thus aid in maintenance planning for such commercial systems. Vehicle location and performance may be optimized for costly applications, such as earth-mining.

SUMMARY OF THE INVENTION

An assembly in accordance with the present invention determines operating parameters of a tire. The assembly includes a tripod sensor mounted within an inner cavity of the tire underneath a crown portion and an innerliner on which the tripod sensor is mounted. The tripod sensor includes a tri-axial accelerometer for creating a circumferential signal for determining slip ratio, a lateral signal for determining a slip angle, and a radial signal for determining load on the tire.

A tire wear state estimation system in accordance with the present invention includes at least one tire supporting a vehicle and a tri-axial sensor mounted to the tire. The tri-axial sensor measuring tire inflation pressure and generating tire inflation pressure data, measuring tire vertical mode frequency and generating tire vertical mode frequency data, generating tire-specific frequency mode coefficients using tire-specific identification data, and calculating an estimation of a tire wear state based upon the tire inflation pressure data, the vertical mode frequency data, and the tire-specific frequency mode coefficients.

According to another aspect of the system, the tri-axial sensor comprises a tire-mounted pressure measuring device operative to measure a tire cavity pressure and transmit the tire inflation pressure data derived from the tire cavity pressure measurement.

According to still another aspect of the system, the tri-axial sensor comprises tire-specific identification data stored therein.

According to still another aspect of the system, measurement of tire vertical mode frequency performed by a wheel-mounted accelerometer or a tire crown-mounted accelerometer.

According to yet another aspect of the system, the tri-axial sensor comprises a correlation model between a tire wear state and a tire vertical mode frequency.

According to yet another aspect of the system, the correlation model comprises a recursive least squares algorithm based on a polynomial model capturing a dependency between a wear state of the tire, tire inflation pressure data, and tire vertical mode frequency of the tire.

A second tire wear state estimation system includes at least one tire supporting a vehicle, a tri-axial sensor affixed to the tire operative to measure a tire cavity pressure and transmit tire inflation pressure data, and tire-specific identification data stored within, and accessible from, the tri-axial sensor. The tri-axial sensor measures tire vertical mode frequency and generates tire vertical mode frequency data, generates tire-specific frequency mode coefficients using the tire-specific identification data and on-vehicle or in-tire measurement of a tire vertical mode frequency, and calculates an estimation of a tire wear state based upon tire inflation pressure data, tire vertical mode frequency data, and tire-specific frequency mode coefficients.

According to another aspect of the second system, measurement of the tire vertical mode frequency is from a wheel-mounted accelerometer or a tire crown-mounted accelerometer.

According to yet another aspect of the second system, the correlation model comprises a recursive least squares algorithm based on a polynomial model capturing a dependency between a wear state of the tire, tire inflation pressure data, and tire vertical mode frequency.

A method of tire wear state estimation in accordance with the present invention includes the steps of affixing a tri-axial sensor to a vehicle-supporting tire, the tri-axial sensor measuring a tire cavity inflation pressure and generating tire inflation pressure data; measuring tire vertical mode frequency and generating tire vertical mode frequency data; generating tire-specific frequency mode coefficients using tire-specific identification data; and calculating an estimation of a tire wear state based upon the tire inflation pressure data, vertical mode frequency data, and tire-specific frequency mode coefficients.

According to another aspect of the method, the method generates tire-specific frequency mode coefficients using on-vehicle or in-tire measurement of a tire vertical mode frequency.

According to still another aspect of the method, the method measures the tire vertical mode frequency from a wheel-mounted accelerometer or a tire crown-mounted accelerometer.

According to yet another aspect of the method, the method calculates an estimation of the tire wear state and employs a correlation model between tire wear state and tire vertical mode frequency.

According to still another aspect of the method, the method configures the correlation model to comprise a recursive least squares algorithm based on a polynomial model capturing a dependency between tire wear state, tire inflation pressure data, and tire vertical mode frequency.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
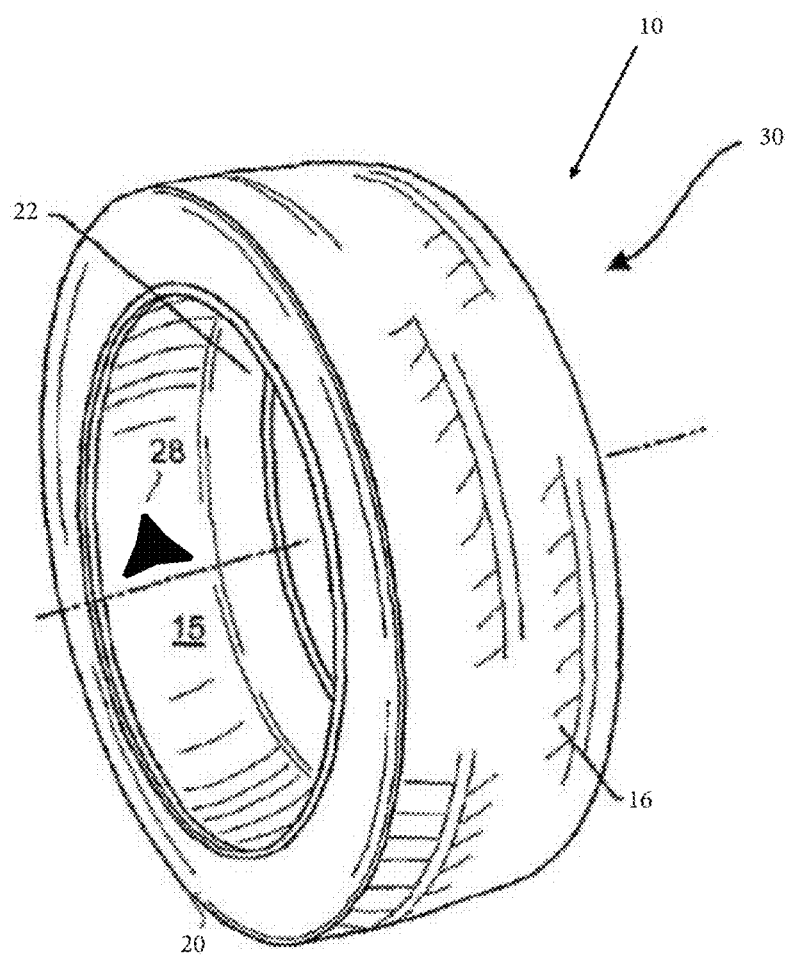
FIG. 1 schematically displays an isometric view of an exemplary tire assembly in accordance with the present invention.

Repeat use of reference characters throughout the present specification and appended drawings is intended to represent same or analogous features or elements of the invention.

DETAILED DESCRIPTION OF EXAMPLES OF THE PRESENT INVENTION

Figure 2:
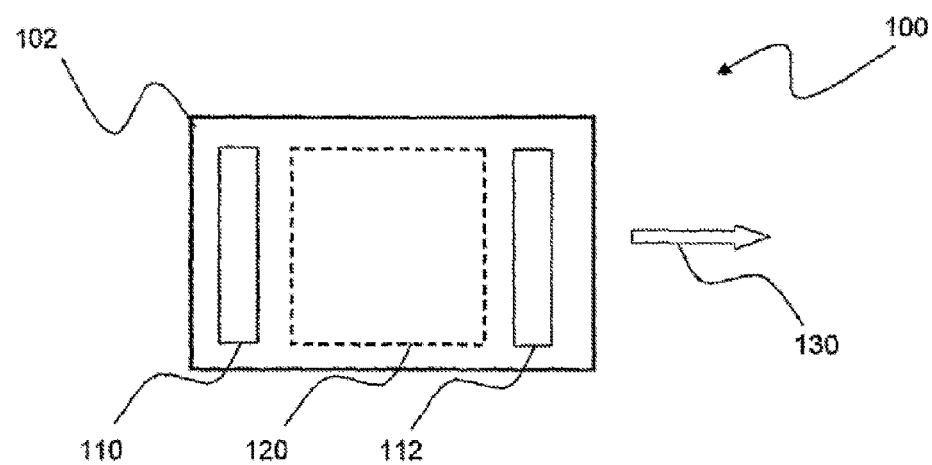
FIG. 2 schematically illustrates an example system employing a pair of piezoelectric sensors.

An assembly in accordance with the present invention may generate tire related signals for determining tire related characteristics, as disclosed in U.S. Pat. Nos. 8,166,809 and 9,050,864, incorporated herein by reference in their entirety. Referring to FIG. 2, an example in-tire multi-element piezoelectric sensor 100 may employ a pair of relatively narrow strip piezoelectric sensors 110, 112 mounted in parallel relationship to each other on either end of a substrate 102. The substrate 102 may be a fiberglass backing board similar to those as printed circuit boards in electronic devices. Exemplary piezoelectric materials may include quartz, barium titanate, cadmium sulfide, lead zirconate titanate (PZT), polyvinylidene fluoride (PVDF), and polyvinyl chloride (PVC).

The piezoelectric sensors 110, 112 may be mounted at a predetermined distance apart, as described below. In the area between the piezoelectric sensors 110, 112, a power harvesting piezoelectric element 120 may be mounted. The power harvesting piezoelectric element 120 may should occupy the maximum possible remaining surface area between the piezoelectric sensors 110, 112 and may also have mounted therewith circuitry for conditioning and storing energy harvested by the power harvesting piezoelectric element 120. Each of the piezoelectric elements 110, 112, 120 may be electrically isolated from the other piezoelectric elements. Suitable piezoelectric materials for use as the power harvesting piezoelectric element 120 may include the same materials described above. The optional energy conditioning and storage circuitry may be similar to that disclosed in U.S. Pat. No. 6,725,713, incorporated herein by reference in its entirety.

The piezoelectric elements 110, 112 may exclusively be signal generators providing tire related signals for later analysis. The power harvesting piezoelectric element 120 may generate similar signals, but such signals may be altered by the electrical load across the element and thus must be taken into consideration. The multi-element piezoelectric sensor 100 may be center mounted on the circumferential centerline of a tire under the crown on the surface of the inner liner and oriented in the rotational direction of the tire, as indicated by arrow 130.

This configuration may provide a time-separable pair of signals such that, by knowing their orientation and precise separation distance, both direction of rolling and surface speed of the tire belt package may be determined by analysis of the sequence of signals generated between the pair of sensors 110, 112 and the lag time between the generated signals. In addition, the time required for one revolution of the rolling tire may be determined from either of the individual piezoelectric sensors 110, 112.

Further, either individual signal piezoelectric sensor 110, 112 may measure the time duration of the contact patch length in either absolute terms or as a ratio of total tire belt length. Tire deflection may then also be calculated. Using the contained tire air pressure amount, the calculated deflection may be analyzed to determine whether the tire is overloaded.

In order to create a tire related "black box", the parameters hereinabove described may be written periodically into a permanent or rewritable memory device in the tire. Thus, a recording of long term tire history, as well as a record of most recent tire history, may be stored and retrieved or even transmitted to a central processor on the vehicle or to a remote location. Such accumulated "black box" data may be used in retread decision making for individual tires by examining total miles run, maximum temperature, minimum pressure, maximum deflection, maximum speed, and/or time or miles spent at a set of running conditions.

If one knows for each tire identification (ID) on the vehicle and, in the same time frame, the inflation pressure, the belt speed, tire angular velocity, and/or contact patch length or deflection or load, one can deduce a combination of relative tire positions sufficiently to identify each tire ID with a specific position on the vehicle. For example, in the case of an eighteen-wheeled truck, any pair of tires mounted dual would have identical angular velocity all the time and therefore steering tires could be identified as the only tires not having a dual partner. During a turn, all tires on one side of the vehicle could see a general increase in load and angular velocity while all tires on the other side of the vehicle would see a general decrease in load and angular velocity. Also during a turn, a comparison of axle speeds should show a general decrease in angular velocity as one progresses from steer axle to the rear of the vehicle due to decreasing turn radius. In very tight turns, inside trailer tires may actually rotate backward.

During braking, the lead axle tires of a tandem would see an increase in load. Other possibilities include selective braking axles through the anti-lock braking system (ABS) and knowing which axle is braking or sorting tires on the basis of presence or absence of drive torque. The relative tire data may be seen by the processor as changes or evolutions in time compared to immediate history or to accumulated history. Such data may be time averaged to improve confidence in position decisions or to confirm prior decisions.

Figure 3:
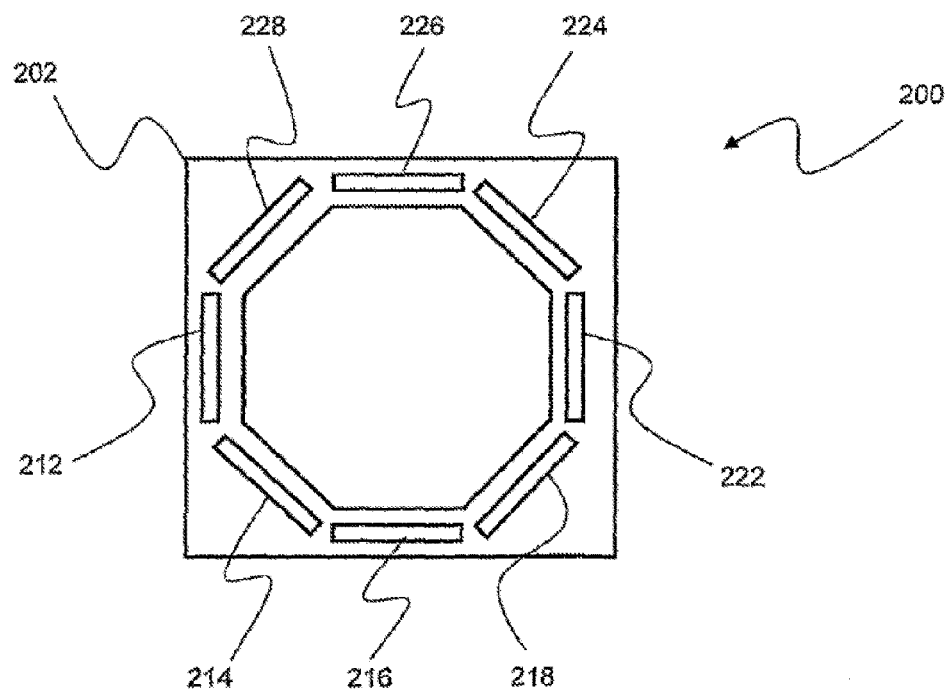
FIG. 3 schematically illustrates another example system employing plural pairs of piezoelectric sensors.

The combination of relative data may be enhanced by a different piezoelectric sensor structure, if it is not possible to control the installation orientation of the multi-element piezoelectric sensor in the tire. Such enhancement may be achieved through use of a second example system, as illustrated in FIG. 3. A multi-element piezoelectric sensor 200 may include four pairs of piezoelectric sensors 212, 222, 214, 224, 216, 226, 218, 228 mounted in a parallel relationship to respective paired piezoelectric sensors and generally in an octagonal configuration around a central axis on a substrate 202. The substrate 202 may be similar to the substrate 102 of FIG. 2, while the paired piezoelectric sensors 212, 222, 214, 224, 216, 226, 218, 228 may be constructed of materials similar to that described with respect to the piezoelectric sensors 110, 112.

With the arrangement of FIG. 3, each of the four opposing pairs of sensors may be interpreted longitudinally, as previously described, with respect to FIG. 2. The pair most nearly longitudinally aligned may be determined by determining the piezoelectric pair having the greatest phase difference or time separation between sense signals. Thus, the pair orthogonal to the identified longitudinal pair may be identified and used to expand the position identification data to include steering response of the tire in combination with the assessed direction of rolling.

With the example multi-element piezoelectric sensor 200 of FIG. 3 installed in each tire of a vehicle and, assuming that a communication system exists such that all tires on the vehicle send various data to a central processing unit on the vehicle, a number of possibilities exist for vehicle control. For example, if data from the multi-element piezoelectric sensor 200 is combined with inflation pressure and temperature signals and sent to a central processor connected to the vehicle's electronic control module (ECM), the data may contribute to the vehicle tire position learning described previously and may also be used to control vehicle operation. Such control may include, but are not limited to, limitations of combined speed, deflection, load, low inflation pressure. A vehicle driver may be given an audible or visible warning and/or the actual vehicle speed may be limited through the EMC in a manner similar to current systems that may limit engine speed based on engine temperature.

Figure 4:
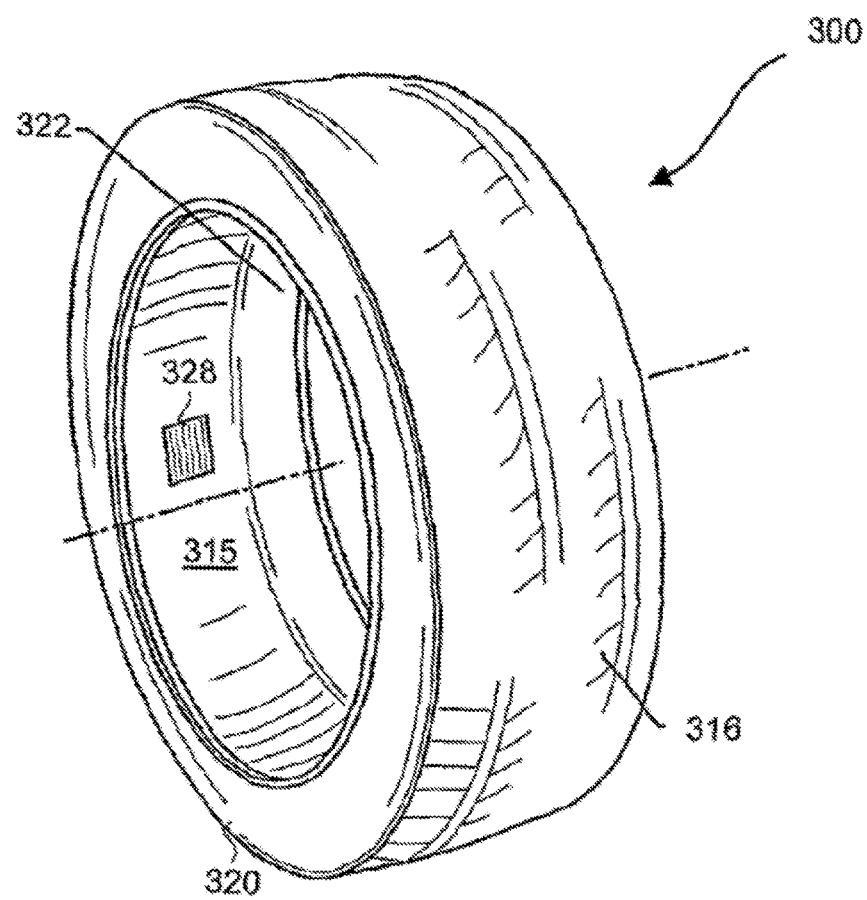
FIG. 4 schematically displays an isometric view of another example system orienting a piezoelectric sensor within a pneumatic tire structure.

Referring now to FIG. 4, another example system may include a multi-element piezoelectric sensor 328 mounted within a tire 300. The tire 300 may include a crown portion 316 having an exterior tread portion, inner and outer sidewall portions 322, 320, respectively, and an inner liner 315 under the crown area 316 on which a multi-element piezoelectric sensor 328 may be mounted.

Figure 5:
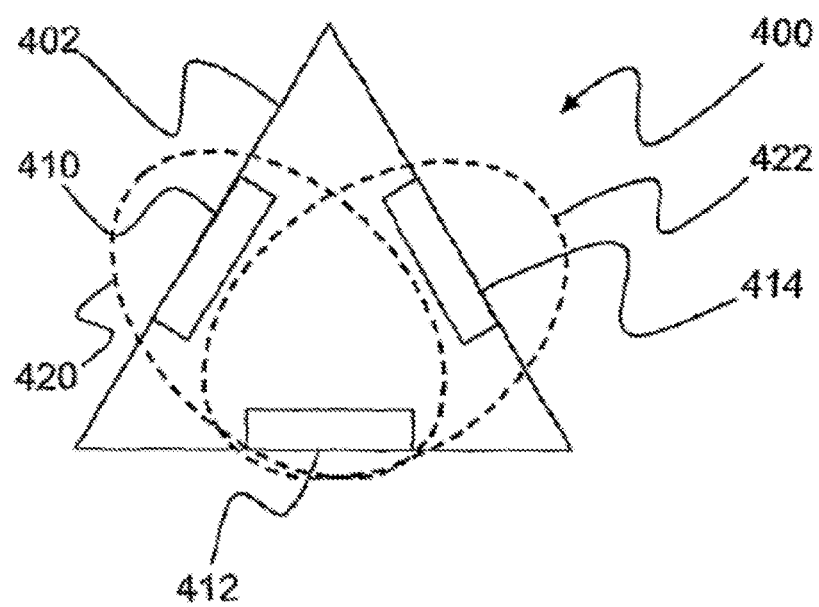
FIG. 5 schematically illustrates another example system employing a shared sensor forming two pairs of sensors from three individual sensors.

It should be appreciated by those of ordinary skill in the art that while the present subject matter has been illustrated and described with reference to a sensor combination with a pneumatic tire, other configurations are envisioned. For example, a sensor may be combined with a non-pneumatic device. It should further be appreciated that the present technology, while requiring the presence of at least one pair of sensors to obtain presently preferred capabilities, is not limited to only a single pair of piezoelectric sensors as illustrated in FIG. 2 or to four pairs of piezoelectric sensors as illustrated in FIG. 3. For example, the sensors may be arranged in a triangular configuration as illustrated in FIG. 5. Moreover, the present technology may be applied using sensors other than the described piezoelectric sensors so long as the physical relationship of paired motion sensitive sensors is maintained.

With reference to FIG. 5, a multi-element piezoelectric sensor 400 may employ a group of three piezoelectric sensors 410, 412, 414 mounted on a substrate 402 in a generally triangular configuration. Two pairs of sensors may be created by including a sensor 412 as an element in both of the pairs. In this manner, the sensors 410, 412 may form a first pair of sensors 420, while the sensors 412, 414 combine to form a second pair of sensors 422. Mounting orientation of the sensor 400 may be determined by analysis of signals from the various sensors 410, 412, 414.

Figure 6:
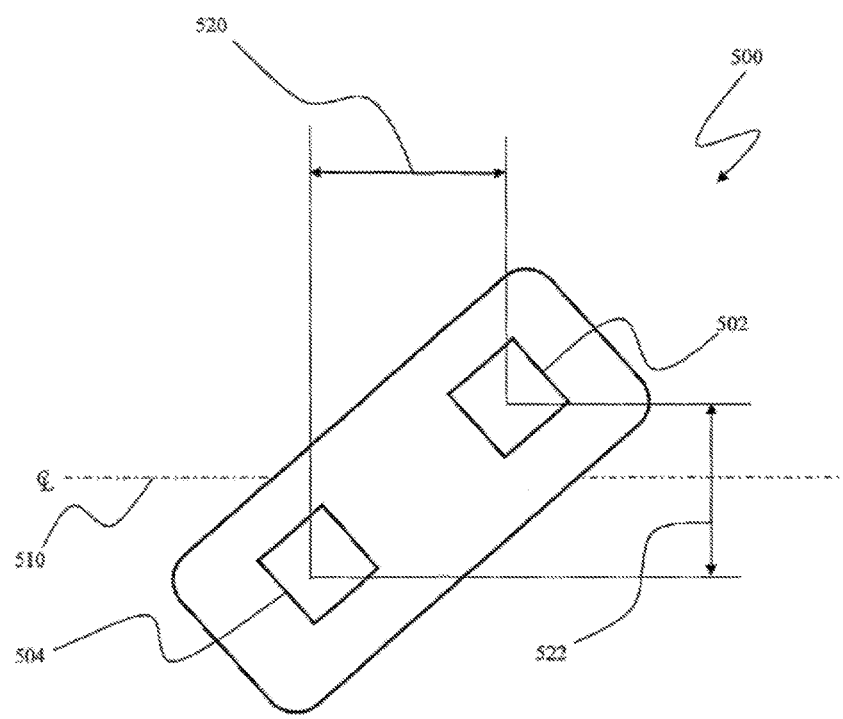
FIG. 6 schematically illustrates another example system employing two pairs of sensors effectively created from a single pair of sensors.

The concept of sharing sensor identification to define plural pairs may be further expanded as illustrated in FIG. 6 so that similar results may be obtained by providing only two sensors. A multi-element piezoelectric sensor 500 may employ a pair of piezoelectric sensors 502, 504. As with the above examples, specific knowledge of the orientation of sensor 500 may be required. If the sensor 500 is positioned at an angle to the centerline 510 of the tire with which the sensor is associated, certain movement generated characteristics may be determined. With the sensor 500 mounted at an angle relative to the tire centerline 510, the difference 520 between the phases of signals produced by the sensors 502, 504 may be used to determine speed and rolling direction of the vehicle. Similarly, the difference 522 in the wavelength produced between the sensors 502, 504 may be employed to determine steer direction and magnitude.

The present invention also contemplates, as previously mentioned, not only the incorporation on the same substrate a power generating and harvesting arrangement, but also the incorporation of other tire electronics elements and sensors. Such elements and sensors may include, but are not limited to, temperature and pressure sensors, surface acoustic wave (SAW) devices, radio frequency identification (RFID) devices, signal and data storage and transmission components, signal reception components, and/or data processing components including microprocessors and microcontrollers.

As shown in FIG. 1, an assembly 10 in accordance with the present invention may support vehicle control systems, including control systems of autonomous vehicles, with its advanced sensor technology. As autonomous vehicles rely on data from other vehicles, drivers, pedestrians, and/or "smart cities", the assembly 10 may exchange information with the vehicle. Such "intelligent" tires 10, 30 may meaningfully contribute to consistent and safe driving in all circumstances, even without human interaction, correction, or control. The assembly 10 may support autonomous vehicle control systems with its advanced sensor technology. As described above, autonomous vehicles may rely on data from other vehicles, other drivers, and possibly from pedestrians and from "smart cities". The assembly 10 may thus optimize this exchange of information with the vehicle.

As shown in FIG. 1, an assembly in accordance with the present invention may include a sensor 28 mounted within a tire 30. The tire 30 may include a crown portion 16 having an exterior tread portion, inner and outer sidewall portions 20, 22, respectively, and an inner liner 15 under the crown portion on which the sensor 28 may be mounted.

The sensor 28 may provide data for determination of weather/road roughness/slipperiness conditions as well as wear condition of the tire 30. The enhanced sensitivity of the sensor 28 may utilize tread and road texture parameters to enhance road sensing capability. For example, data from the sensor 28 may be utilized to optimize speed and braking performance. The assembly 10 may sense road conditions, including both surface and weather conditions, through a microchip inside the tire 30, as well as a specially designed tread. For autonomous vehicles, detection of aquaplaning and friction becomes particularly useful. For manual vehicles, the driver typically determines road conditions. If the tire tread is worn, if the road surface is slippery, and/or if the wrong season tires are on the vehicle, vehicle safety systems may be less effective.

Autonomous vehicles thus may undertake the functions of the driver. Such vehicle may be required to derive tire/road friction automatically. Autonomous cars' central computer system may take into account tire operating conditions and be able to automatically refine the vehicle's control algorithms to deliver an improved driving performance. The sensor may have a tripod shape with multiple arms and a multiple arm chip. The tripod shape may enhance the fixation of the sensor 28 to the tire 30. The tripod sensor 28 may integrate a plurality of sensors up to the terminal end of the arms to enhance road sensing feel on a full tire width, instead of just a single point. The sensor 28 may be a tri-axial accelerometer for creating a circumferential signal, a lateral signal, and a radial signal. The circumferential signal may determine a slip ratio for the tire 30. The lateral signal may determine a slip angle for the tire 30. The radial signal may determine a load on the tire 30.

Wear estimation methods may use the sensor data for utilizing vibration mode frequency shift as an indicator of the tire wear. Tire wear state may be recursively estimated by using a recursive least squares (RLS) algorithm formulated based on a polynomial model, capturing the dependencies between the tire wear state, inflation pressure, and/or the tire vertical mode frequency. Inputs for the RLS algorithm may include tire inflation pressure, tire ID (required for using tire specific model coefficients), and the tire vertical mode frequency. Tire inflation pressure and tire ID information may available from other sensors. Tire vertical mode frequency data may be obtained by extracting vertical mode frequency from the vertical acceleration signal of a crown mounted accelerometer.

While the present invention has been described in detail with respect to specific examples thereof, it will be appreciated that those skilled in the art, upon attaining an understanding of the foregoing, may readily produce alterations to, variations of, and equivalents to such examples. Accordingly, the scope of the present invention is by way of example rather than by way of limitation, and the subject disclosure does not preclude inclusion of such modifications, variations, and/or additions to the present invention as would be readily apparent to one of ordinary skill in the art.

What is claimed:

1. A tire wear state estimation system comprising:
   at least one tire supporting a vehicle;
   a tri-axial sensor mounted to the tire, the tri-axial sensor measuring tire inflation pressure and generating tire inflation pressure data, measuring tire vertical mode frequency and generating tire vertical mode frequency data, generating tire-specific frequency mode coefficients using tire-specific identification data, and calculating an estimation of a tire wear state based upon the tire inflation pressure data, the vertical mode frequency data, and the tire-specific frequency mode coefficients.

2. The tire wear state estimation system of claim 1 wherein the tri-axial sensor comprises a tire-mounted pressure measuring device operative to measure a tire cavity pressure and transmit the tire inflation pressure data derived from the tire cavity pressure measurement.

3. The tire wear state estimation system of claim 2 wherein the tri-axial sensor comprises tire-specific identification data stored therein.

4. The tire wear state estimation system of claim 3 wherein tire-specific frequency mode coefficients are generated by the tri-axial sensor using on-vehicle or in-tire measurement of a tire vertical mode frequency.

5. The tire wear state estimation system of claim 4 wherein measurement of tire vertical mode frequency performed by a wheel-mounted accelerometer or a tire crown-mounted accelerometer.

6. A tire wear state estimation system comprising:
   at least one tire supporting a vehicle;
   a tri-axial sensor affixed to the tire operative to measure a tire cavity pressure and transmit tire inflation pressure data; and
   tire-specific identification data stored within, and accessible from, the tri-axial sensor, the tri-axial sensor measuring tire vertical mode frequency and generating tire vertical mode frequency data, generating tire-specific frequency mode coefficients using the tire-specific identification data and on-vehicle or in-tire measurement of a tire vertical mode frequency, and calculating an estimation of a tire wear state based upon tire inflation pressure data, tire vertical mode frequency data, and tire-specific frequency mode coefficients.

7. The tire wear state estimation system of claim 6 wherein measurement of the tire vertical mode frequency is from a wheel-mounted accelerometer or a tire crown-mounted accelerometer.

8. A method of tire wear state estimation comprising:
   affixing a tri-axial sensor to a vehicle-supporting tire, the tri-axial sensor measuring a tire cavity inflation pressure and generating tire inflation pressure data;
   measuring tire vertical mode frequency and generating tire vertical mode frequency data;
   generating tire-specific frequency mode coefficients using tire-specific identification data; and
   calculating an estimation of a tire wear state based upon the tire inflation pressure data, vertical mode frequency data, and tire-specific frequency mode coefficients.

9. The method of claim 8 further comprising generating tire-specific frequency mode coefficients using on-vehicle or in-tire measurement of a tire vertical mode frequency.

10. The method of claim 9 further comprising measuring the tire vertical mode frequency from a wheel-mounted accelerometer or a tire crown-mounted accelerometer.

11. The method of claim 8 further comprising calculating an estimation of the tire wear state includes employing a correlation model between tire wear state and tire vertical mode frequency.

12. The method of claim 11 further comprising configuring the correlation model to comprise a recursive least squares algorithm based on a polynomial model capturing a dependency between tire wear state, tire inflation pressure data, and tire vertical mode frequency.

* * * * *